US00PP23835P3

(12) United States Plant Patent
Danziger

(10) Patent No.: US PP23,835 P3
(45) Date of Patent: Aug. 13, 2013

(54) ***SUTERA* PLANT NAMED 'DANCOP37'**

(50) Latin Name: *Sutera cordata*
Varietal Denomination: DANCOP37

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 190 days.

(21) Appl. No.: 13/066,204

(22) Filed: Apr. 7, 2011

(65) Prior Publication Data

US 2012/0260385 P1 Oct. 11, 2012

(51) Int. Cl.
*A01H 5/00* (2006.01)

(52) U.S. Cl.
USPC ..... Plt./485

(58) Field of Classification Search
USPC ..... Plt./485
See application file for complete search history.

*Primary Examiner* — June Hwu
*Assistant Examiner* — Louanne Krawczewicz Myers
(74) *Attorney, Agent, or Firm* — Cassandra Bright

(57) ABSTRACT

A new and distinct *Sutera* cultivar named 'DANCOP37' is disclosed, characterized by extra large blue flowers, early and abundant flowering. The new variety has a semi-trailing, compact growth habit and moderate vigor. The new variety is a *Sutera,* normally produced as an outdoor garden or container plant.

2 Drawing Sheets

Figure 1:
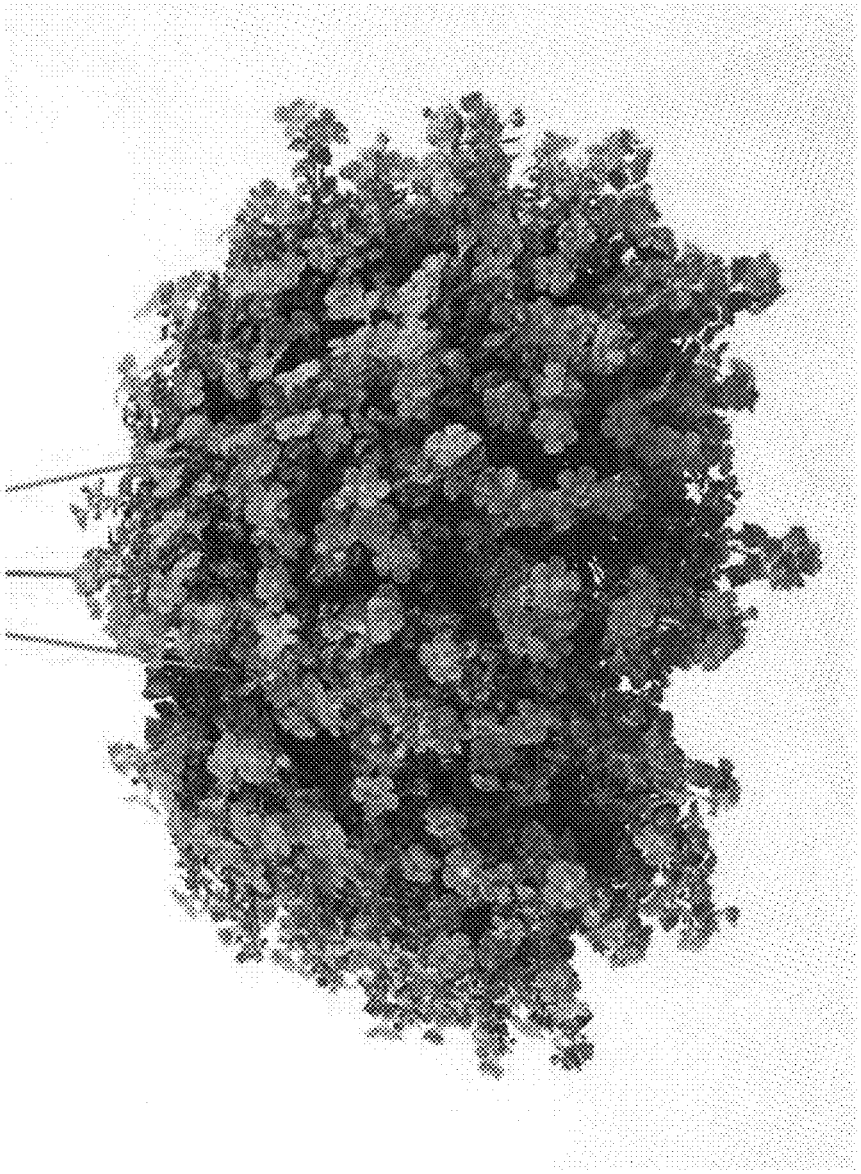

Latin name of the genus and species: *Sutera cordata.*
Variety denomination: 'DANCOP37'.

BACKGROUND OF THE INVENTION

The new *Sutera* cultivar is a product of a planned breeding program conducted by the inventor, Gavriel Danziger, in Moshav Mishmar Hashiva, Israel. The objective of the breeding program was to produce new *Sutera* varieties for ornamental commercial applications. The cross resulting in this new variety was made during June 2007.

The seed parent is the unpatented, proprietary seedling variety referred to as *Sutera cordata* 'Cv-07-577' The pollen parent is unknown, as the crossing resulting in 'DANCOP37' was an open pollination, with unidentifiable pollen parents. The new variety was discovered in April 2008 by the inventor in a group of seedlings resulting from the 2007 crossing, in a research greenhouse in Moshav Mishmar Hashiva, Israel.

Asexual reproduction of the new cultivar 'DANCOP37' by vegetative cuttings was first performed at a research greenhouse in Moshav Mishmar Hashiva, Israel in May 2008 and has shown that the unique features of this cultivar are stable and reproduced true to type in successive generations.

SUMMARY OF THE INVENTION

The cultivar 'DANCOP37' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANCOP37' These characteristics in combination distinguish 'DANCOP37' as a new and distinct *Sutera* cultivar:

1. Semi-trailing, compact growth habit
2. Extra large blue flowers
3. Very free branching plants 4. Early, abundant flowering
5. Moderately vigorous growth Plants of the new cultivar 'DANCOP37' are similar to plants of the seed parent, *Sutera cordata* 'Cv07-577' in most horticultural characteristics, however, plants of the new cultivar 'DANCOP37' have a somewhat less trailing, more compact plant habit, larger flowers of a different color, and more branches per plant. Additionally, the new cultivar begins flowering earlier, produces more flowers, and slightly less vigorous plants than the seed parent.

COMMERCIAL COMPARISON

Plants of the new cultivar 'DANCOP37' are comparable to the variety *Sutera* 'DANCOP24' U.S. Plant Pat. No. 19,343. The two *Sutera* varieties are similar in most horticultural characteristics however, the new variety 'DANCOP37' differs in having different color flowers, and an overall more compact plant habit. Additionally, the new variety has larger leaves than 'DANCOP24'.

Plants of the new cultivar 'DANCOP37' can also be compared to the commercial variety *Sutera* 'DANGUL14' U.S. Plant Pat. No. 18,194. These varieties are similar in most horticultural characteristics, however 'DANCOP37' has different color flowers and slightly more branching than 'DANGUL14'. Additionally, plants of 'DANCOP37' grow somewhat less vigorously than DANGUL14.

BRIEF DESCRIPTION OF THE PHOTOGRAPHS

The accompanying photograph in FIG. 1 illustrates in full color a typical plant of 'DANCOP37' grown in a greenhouse, in a 13 cm basket. Age of the plant photographed is approximately 3 months from a rooted cutting.

Figure 2:
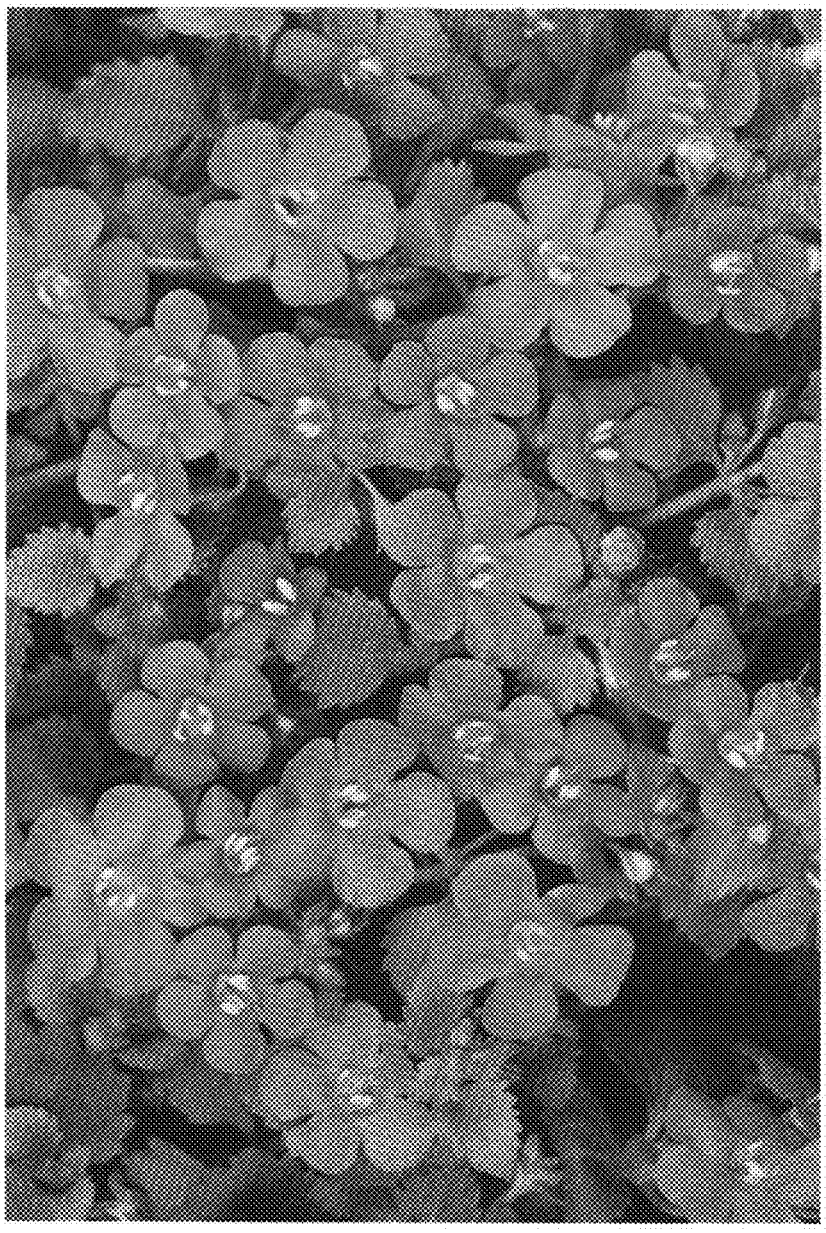

FIG. 2 illustrates in full color a close up of a typical bloom of 'DANCOP37'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DANCOP37' plants grown in a greenhouse during Winter and Spring in Moshav Mishmar Hashiva, Israel. Plants were approximate 20 weeks old from a rooted cutting. The growing temperature ranged from 15° C. to 26° C. during the day and from 13° C. to 16° C. during the night. General light conditions are bright, normal sunlight. Measurements and numerical values represent averages of typical plant types.
Botanical classification: *Sutera cordata* 'DANCOP37 '.

PROPAGATION

Time to initiate roots: About to 10 days at approximately 20° C.
Root description: Fine, fibrous.

PLANT

Growth habit: Semi-trailing, compact.
Pot size of plant described: 13 cm.
Height: Approximately 10 cm.
Plant spread: Approximately 40 cm.
Growth rate: Moderate vigor.
Branching characteristics: Very free branching.
Length of primary lateral branches: Approximately 30 cm.
Diameter of lateral branches: Approximately 0.2 cm.
Quantity of primary lateral branches: Approximately 10.
Characteristics of primary lateral branches:
- *Form*.—Cylindrical.
- *Diameter*.—Approximately 0.2 cm.
- *Color*.—Near RHS Green 138 B.
- *Texture*.—Velvety.
- *Strength*.—Strong.

Internode length: Approximately 2 cm.

FOLIAGE

Leaf:
- *Arrangement*.—Opposite, petiolate.
- *Quantity*.—Approximately 50 per branch.
- *Average length*.—3.5 cm.
- *Average width*.—2.5 cm.
- *Shape of blade*.—Ovate.
- *Apex*.—Acute.
- *Base*.—Acuminate.
- *Margin*.—Serrate.
- *Texture of top surface*.—Velvety.
- *Pubescence*.—Slightly pubescent on upper and lower surfaces.
- *Aspect*.—Flat.
- *Color*.—Young foliage upper side: RHS Green 137 C. Young foliage under side: RHS Green 137 D. Mature foliage upper side: RHS Green 137 A. Mature foliage under side: RHS Green 137 B.
- *Venation*.—Type: Pinnate. Venation color upper side: RHS Green 137 A. Venation color under side: RHS Green 137 B.
- *Petiole*.—Length: Approximately 0.5 cm. Diameter: Approximately 0.1 cm. Color: RHS Green 137 A.
- *Texture*.—Slightly velvety.

FLOWER

Natural flowering season: All year round under controlled greenhouse conditions. Spring through Summer flowering in temperature climates.
Days to flowering from rooted cutting: About 45.
Inflorescence and flower type and habit: Axillary, solitary salverform single flowers.
Quantity of flowers per branch: Average of 5 to 10.
Rate of flower opening: 3 to 5 days from bud to fully opened flower.
Flower longevity on plant: About 7 days.
Persistent or self-cleaning: Persistent.
Bud:
- *Shape*.—Spatulate.
- *Length*.—About 1.2 cm.
- *Diameter*.—About 0.6 cm.
- *Color*.—RHS Violet-Blue 93 C.

Flower size:
- *Diameter*.—About 2.9 cm.
- *Length*.—About 1.5 cm.
- *Corolla tube diameter*.—About 0.5 cm.
- *Corolla tube length*. —About 1.1 cm.

Corolla/petals:
- *Arrangement*.—Symmetric.
- *Lobe length*.—About 1.0 cm.
- *Lobe width*.—About 1.2 cm.
- *Quantity*.—5.
- *Texture*.—Velvety, upper and lower surfaces.
- *Lobe apex*.—Rounded.
- *Lobe shape*.—Rounded.
- *Margin*.—Entire.
- *Color*.—When opening: Upper surface: RHS Violet N 88 A. Lower surface: RHS Violet N 88 C. Fully opened: Upper surface: RHS. Violet N 88 B. Lower surface: RHS Violet N 88 C. Corolla tube color: Throat: RHS Yellow-Orange 21 A. Outer tube: RHS Violet N 88 C.

Calyx/sepals:
- *Quantity per flower*.—5.
- *Shape*.—Linear.
- *Length*.—About 0.6 cm.
- *Width*.—About 0.1 cm.
- *Apex*.—Acute.
- *Base*.—Fused.
- *Margin*.—Entire.
- *Texture*.—Slightly velvety upper and lower surfaces.
- *Color*.—Upper Surface: RHS Green 137 B. Lower Surface: RHS Green 137 B.

Peduncle: None.
Pedicel:
- *Length*.—Approximately 1 cm.
- *Diameter*.—Approximately 0.1 cm.
- *Color*.—Near RHS Green 138 B.
- *Orientation*.—Slanted upward and outward.
- *Pubescence*.—Slightly pubescent.

Fragrance: None.

REPRODUCTIVE ORGANS

Stamens:
- *Number*.—4.
- *Filament length*.—Approximately 1 cm.

Anthers:

*Shape*.—Cylindrical.

*Length*.—Approximately 0.1 cm.

*Color*.—RHS Yellow-Orange 21 B.

*Pollen*.—Color: RHS Yellow-Orange 21 A. Quantity: Abundant.

Pistil:

*Number*.—1.

*Length*.—About 1.4 cm.

*Style*.—Length: about 1.0 cm. Color: RHS Green-Yellow 1 C.

*Stigma*.—Shape: Undulate. Color: RHS Green-Yellow 1 B. Ovary Color: RHS Green 137 C.

OTHER CHARACTERISTICS

Seeds and fruits: About 20 elliptic, small (1 mm long) seeds colored near RHS Grey-Brown 199D per one elliptic Brown 200 D capsule.

Disease/pest resistance: Neither resistance nor susceptibility to pathogens and pests common to *Sutera* have been observed.

Temperature tolerance: The new variety tolerates temperatures between 5 to 40° C.

What is claimed is:

1. A new and distinct cultivar of *Sutera* plant named 'DANCOP37' as herein illustrated and described.

* * * * *